United States Patent [19]
Racz

[11] Patent Number: 5,490,845
[45] Date of Patent: Feb. 13, 1996

[54] R-X SAFETY CATHETER

[76] Inventor: Gabor J. Racz, 4412 17th St., Lubbock, Tex. 79416

[21] Appl. No.: 309,244

[22] Filed: Sep. 20, 1994

[51] Int. Cl.$^6$ ..................................................... A61M 5/32
[52] U.S. Cl. ......................... 604/266; 604/267; 604/280
[58] Field of Search ................................. 604/266, 27, 96, 604/51, 53, 52, 93, 236, 256, 264, 267, 268, 270, 272, 273, 280

[56] References Cited

U.S. PATENT DOCUMENTS

| | | |
|---|---|---|
| 3,856,009 | 12/1974 | Winnie . |
| 4,194,513 | 3/1980 | Rhine et al. .............................. 604/256 |
| 4,518,383 | 5/1985 | Evans . |
| 4,610,671 | 9/1986 | Luther ..................................... 604/264 |
| 4,650,472 | 3/1987 | Bates . |
| 4,863,424 | 9/1989 | Blake, III et al. ....................... 604/103 |
| 5,084,022 | 1/1992 | Claude . |
| 5,106,369 | 4/1992 | Christmas ................................ 604/51 |
| 5,106,376 | 4/1992 | Mononen et al. . |
| 5,114,401 | 5/1992 | Stuart et al. ............................. 604/53 |
| 5,129,889 | 7/1992 | Hahn . |
| 5,232,442 | 8/1993 | Johnson et al. . |
| 5,263,947 | 11/1993 | Koy ......................................... 604/331 |
| 5,348,541 | 9/1994 | Lyell ....................................... 604/272 |

FOREIGN PATENT DOCUMENTS 2380034  2/1977  France .

*Primary Examiner*—Corrine M. Maglione
*Assistant Examiner*—N. Kent Gring
*Attorney, Agent, or Firm*—Trask, Britt & Rossa

[57] ABSTRACT

A flexible catheter comprising a flexible, cylindrical member having a bore therethrough and including an intra-luminal chord within the wall of the cylindrical member or the lumen of the cylindrical member to prevent the collapse thereof and facilitate the removal of broken portions thereof.

6 Claims, 3 Drawing Sheets

R-X SAFETY CATHETER

BACKGROUND OF THE INVENTION

1. Field of the Invention

This invention is related to catheters for introducing fluids into body cavities. More specifically, this invention relates to small diameter catheters for introducing medications into the spinal canal, spinal space, epidural space, blood vessels, body cavities, and the like.

2. State of the Art

Small diameter catheters are used to introduce medication into the spinal canal, spinal space, epidural space, blood vessels, body cavities and the like. Due to their uni-wall construction when undergoing repetitive movement while being subjected to body heat, such small diameter catheters have a tendency to migrate to other body cavities or to kink thereby preventing the flow of medication therethrough. Such problems can be particularly troublesome when a catheter is used within the spinal canal. In the event of migration of the catheter any kinking of the catheter will preclude aspiration and seeing evidence of such migration due to the closure of the lumen of the catheter and the attendant inability to withdraw blood or spinal fluid. Typical prior art catheter placement units for small diameter catheters are shown in U.S. Pat. Nos. 3,856,009; 4,518,383; 4,650,472; 5,084,022; 5,106,376; 5,129,889; 5,213,578; and 5,232,442.

Another problem associated with the use of such small diameter catheters is their susceptibility to breaking and, possibly, leaving portions thereof remaining in a body cavity. Removal of such broken portions of the catheter may be difficult or impossible.

SUMMARY OF THE INVENTION

The present invention relates to a catheter which prevents occlusion thereof to allow the flow of fluids therethrough and allows the removal of broken portions thereof from the spinal canal, spinal space, epidural space, blood vessels, body cavities and the like during use. The present invention is directed to a flexible catheter comprising a flexible cylindrical member having a bore therethrough and including one or more intra-luminal chord within the wall of the cylindrical member or the lumen of the cylindrical member to prevent the collapse thereof and facilitate the removal of broken portions thereof.

The present invention will be better understood when the drawings are taken in conjunction with the description of the invention hereafter.

DETAILED DESCRIPTION OF THE ILLUSTRATED EMBODIMENT

Figure 1:
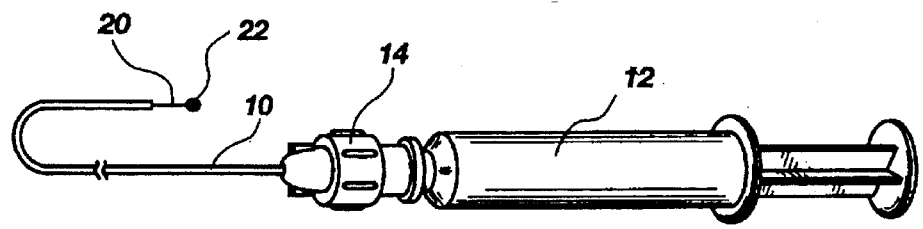
FIG. 1 is an embodiment of the present invention for use with a syringe.

Referring to drawing FIG. 1, the catheter 10 of the present invention is shown in conjunction with a syringe 12 having a connector hub 14 thereon. As shown, the catheter 10 comprises a hollow cylindrical member having an intra-luminal member 20 extending therethrough terminating at enlarged end 22 thereof.

Figure 2:
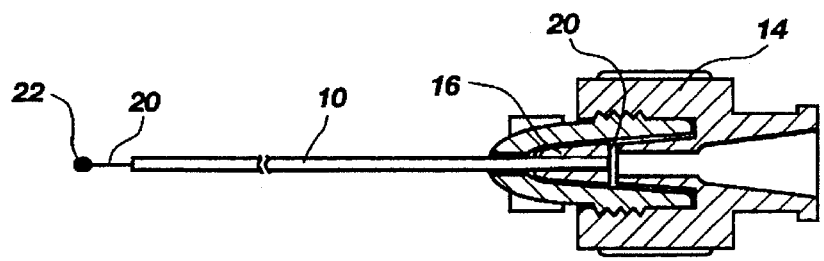
FIG. 2 is an embodiment of the present invention shown in FIG. 1 with a portion of the connector hub to syringe shown in cross-section.

Referring to drawing FIG. 2, the connector hub 14 is shown in conjunction with the catheter 10. The catheter 10 is retained within connector hub 14 via bushing 16. Typically, a portion of the intra-luminal member 20 extends beyond bushing 16 and is trapped between bushing 16 and the male portion 18 of connector 14 thereby securing the intra-luminal member 20 within connector 14.

Figure 3:
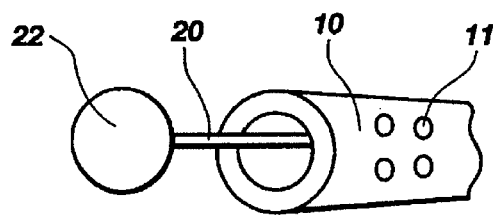
FIG. 3 is an enlarged view of an end of the present invention.

Referring to drawing FIG. 3, a portion of the catheter 10 is shown. The intra-luminal member 20 extends beyond the end of catheter 10 any desired distance terminating in an enlarged end 22 being greater in diameter than the lumen of catheter 10. In this manner, if a portion of the catheter 10 breaks off in a patient, the broken portion of the catheter 10 may be retrieved from the patient by pulling on the intra-lumen member 20 thereby causing enlarged end 22 to abut the end of the piece of broken catheter causing, in turn, the broken piece to be retrieved. As shown, the intra-lumen member 20 has a substantially circular cross-sectional shape as well as enlarged end having a spherical shape. However, any desired cross-sectional shape for intra-lumen member 20 may be used. A spherical shape enlarged end for intra-luminal member 20 as it acts as a guide for the catheter 10 and helps minimize damage to the tissue surrounding the area into which the catheter 10 is being inserted.

The intra-lumen member 20 may be made of metal or other electrically conductive material. A current applied to the intra-lumen member 20 may serve to verify the location of the tip of the catheter 10. Further, a conductive intra-lumen member 20 may be used to provide electrical stimulation to the spinal cord or nerve cells that come in contact with the enlarged end 22.

It should be noted that in addition to allowing the retrieval of any broken portion of catheter 10 from a patient, intra-luminal member 20 additionally allows the flow of fluid through the lumen of the catheter 10 when bent or kinked by preventing the complete closure of the lumen. By having intra-lumen member 20 in the catheter 10 even if bent or kinked, the intra-luminal member 20 keeps the catheter 10 from being completely closed to thereby provide a small fluid passageway around the member 20 through the lumen. Additionally, the catheter 10 includes a plurality of apertures or holes 11 therein in the distal end so that should the enlarged end 22 block the lumen of the catheter 10 fluid may pass through holes 11.

Figure 4:
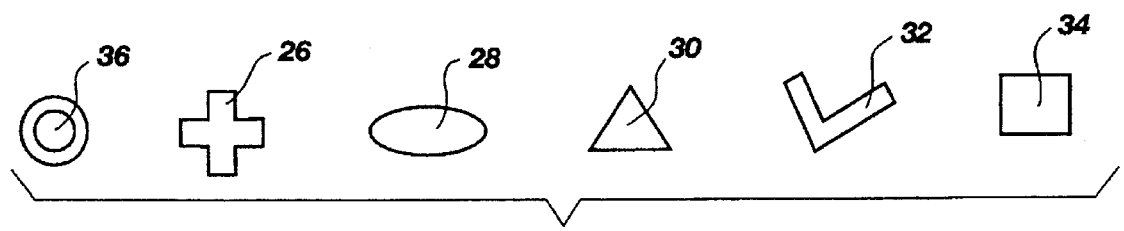
FIG. 4 is a view of different cross-sectional shapes of the chord of the present invention.

Referring to drawing FIG. 4, various cross-sectional shapes for the intra-luminal member 20 are shown. The intra-luminal member 20 may have a symmetrical cross shape or X shape, cross-sectional shape 26, if desired, to allow greater fluid flow area around member 20. Alternately, the intra-luminal member 20 may have an elliptical, cross-sectional shape 28; triangular, cross-sectional shape 30; V-shaped, cross-sectional shape 32; rectangular, cross-sectional shape 34; or annular, cross-sectional shape 36.

Figure 5:
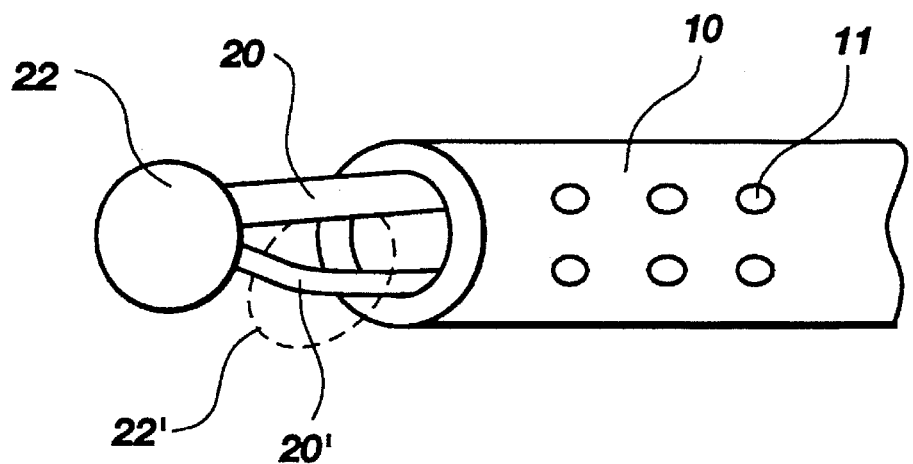
FIG. 5 is an enlarged view of an end of another embodiment of the present invention having a plurality of intra-luminal chords.

Referring to drawing FIG. 5, a portion of a catheter 10 having holes 11 therein is shown. The catheter 10 includes a plurality of intra-luminal members 20 and 20' therein terminating in an enlarged end 22 being greater in diameter than the lumen of catheter 10. As shown, both the intra-lumen member 20 and the intra-lumen member 20' have substantially circular cross-sectional shapes terminating in the enlarged spherical end 22. As previously stated, the spherical shape of enlarged end 22 acts as a guide for the catheter 10 and helps minimize damage to the tissue surrounding the area into which the catheter 10 is being inserted. As shown, the intra-lumen members 20 and 20' may be of different sizes and/or material composition. Further, if desired, each intra-lumen member may terminate in an enlarged spherical end, such as shown in broken lines 22' for intra-lumen member 20'.

Figure 6:
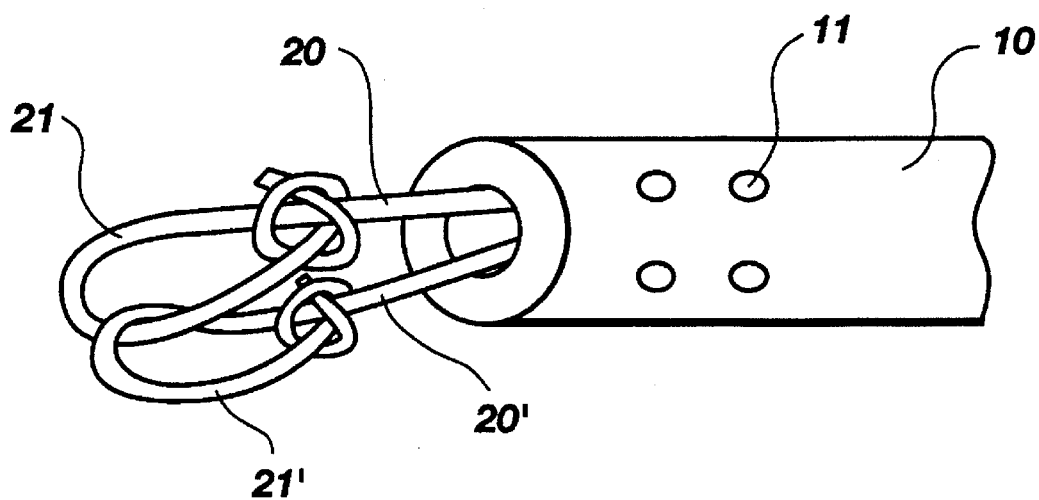
FIG. 6 is an enlarged view of an end of another embodiment of the present invention having a plurality of intra-luminal chords terminated in interlocking loops.

Referring to drawing FIG. 6, a portion of a catheter 10 having holes 11 therein is shown. The catheter 10 includes a plurality of intra-luminal members 20 and 20' therein terminating in interlocking loops 21 and 21' respectively, the loops and knots of the intra-luminal members 20 and 20' being of sufficient size to prevent the intra-luminal members 20 and 20' from being pulled into the lumen of the catheter 10. Any suitable type knot may be used to fore the loops 21 and 21' on the members 20 and 20'.

Referring to drawing FIGS. 3, 4, 5 and 6, the catheter 10 may be formed of any suitable material as well as intra-luminal member 20. Such suitable materials are nylon, polymers, plastic, metals, silicone embedded materials, Silastic tubing, etc. If desired, the catheter 10 may be made of translucent material or material opaque to x-rays, radioactive materials, and the like. If desired, member 20 may be molded into the wall of catheter 10 during manufacture. Additionally, the intra-luminal member 20 may be treated with non-thrombogenic materials, such as heparin, to prevent occlusion of the catheter 10 when for use in long-term, indwelling cannulas or catheters. Furthermore, the catheter or cannula 10 may be made anti-septic by special treatment with materials such as silver nitrate, chloro-hexadine, silver-diazine, etc.

The intra-luminal member 20 may comprises a fiber optic member having an enlarged end thereon. In this manner, a camera may be connected to the intra-luminal member 20 for viewing the area where the end of the catheter is located.

Figure 7:
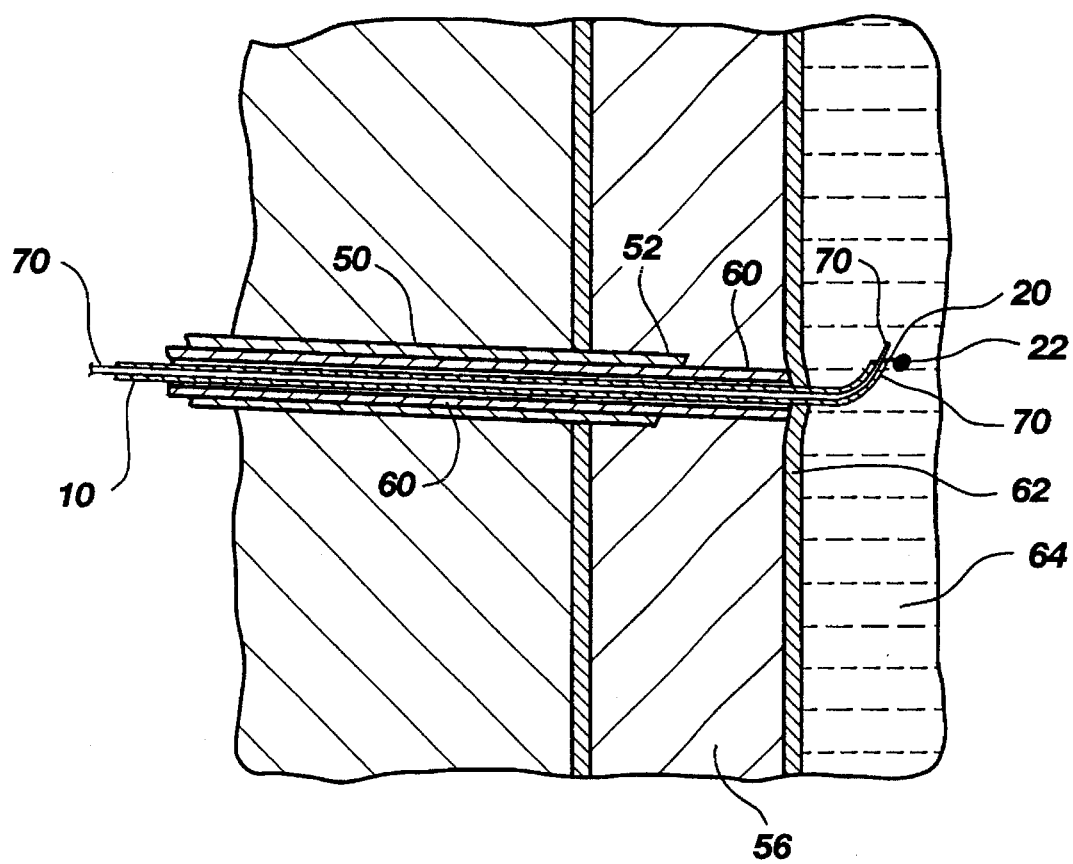
FIG. 7 is a cross-sectional view of an anesthesia assembly for use with the present invention.
Figure 8:
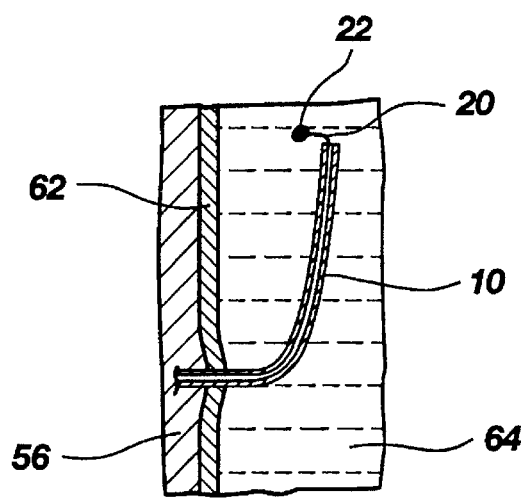
FIG. 8 is a cross-sectional view of an anesthesia assembly and a portion of the present invention in use.

Referring to drawing FIGS. 7 and 8, a catheter 10 of the present invention is shown in use in the spinal canal of a patient. An epidural needle 50 is inserted at a slight angle to a patient's skin until point 52 passes through ligament 54 and into the epidural space 56. Once the epidural space 56 has been reached by point 52 of needle 50, an introducer 60 is inserted through the lumen of needle 50 until it abuts dura wall 62. Subsequently, the catheter 10 with styler 70 in place is inserted through the lumen of introducer 60. The stylet 70 penetrates the dura wall by spreading the fibers thereof. Both the catheter 10 and stylet 70 are advanced into the subarachnoid space 64. Stylet 70 is then removed, and a syringe used to withdraw spinal fluid to confirm the location of the end of catheter 10. The distal end of the catheter 10 is maintained outside the patient's body and may be coupled to any desired tubing, syringe, etc. As can be readily seen, if any portion of catheter 10 in the patient is broken, it can be retrieved easily by pulling on intra-luminal member 20. Also, if the catheter 10 is kinked, the intra-luminal member 20 will allow the flow of fluids through the catheter 10.

It will be understood that the foregoing invention will be equally applicable in those instances where catheters are used to drain fluids and kinking and clotting are potential problems.

What is claimed is:

1. A safety catheter facilitating the flow of fluids to and from a body and the safe removal of said catheter from said body, said safety catheter comprising:

an elongated cylindrical member having a bore therethrough; and at least one retrieval member extending throughout said bore and extending from each end of said cylindrical member, a first portion of said retrieval member extending beyond an end of said cylindrical member terminating in an end having a greater diameter than said bore of said cylindrical member to prevent said end from entering said bore of said cylindrical member wherein said retrieval member maintains said bore of said cylindrical member open to allow said flow of said fluids to and from said body and the safe retrieval of said cylindrical member from said body and wherein said retrieval member comprises a loop formed on said first portion of said retrieval member extending beyond an end of said cylindrical member to prevent passage of said first portion through said cylindrical member.

2. A safety catheter facilitating the flow of fluids to and from a body and the safe removal of said catheter from said body, said safety catheter comprising:

an elongated cylindrical member having a bore therethrough; and at least one retrieval member extending throughout said bore and extending from each end of said cylindrical member, a first portion of said retrieval member extending beyond an end of said cylindrical member terminating in an end having a greater diameter than said bore of said cylindrical member to prevent said end from entering said bore of said cylindrical member wherein said retrieval member maintains said bore of said cylindrical member open to allow said flow of said fluids to and from said body and the safe retrieval of said cylindrical member from said body and wherein said retrieval member comprises an elongated, annular member having a bore therethrough.

3. A safety catheter facilitating the flow of fluids to and from a body and the safe removal of said catheter from said body, said safety catheter comprising:

an elongated cylindrical member having a bore therethrough; and at least one retrieval member extending throughout said bore and extending from each end of said cylindrical member, a first portion of said retrieval member extending beyond an end of said cylindrical member terminating in an end having a greater diameter than said bore of said cylindrical member to prevent said end from entering said bore of said cylindrical member wherein said retrieval member maintains said bore of said cylindrical member open to allow said flow of said fluids to and from said body and the safe retrieval of said cylindrical member from said body and wherein said retrieval member comprises at least two elongated, solid members, each solid member terminating in an enlarged end having a greater diameter than said bore of said cylindrical member.

4. A safety catheter facilitating the flow of fluids to and from a body and the safe removal of said catheter from said body, said safety catheter comprising:

an elongated cylindrical member having a bore therethrough; and at least one retrieval member extending throughout said bore and extending from each end of said cylindrical member, a first portion of said retrieval member extending beyond an end of said cylindrical member terminating in an end having a greater diameter than said bore of said cylindrical member to prevent said end from entering said bore of said cylindrical member wherein said retrieval member maintains said bore of said cylindrical member open to allow said flow of said fluids to and from said body and the safe retrieval of said cylindrical member from said body and wherein said retrieval member comprises at least two elongated, solid members, each solid member terminating in a single common enlarged end to both said members, said common enlarged end having a greater diameter than said bore of said cylindrical member.

5. A safety catheter facilitating the flow of fluids to and from a body and the safe removal of said catheter from said body, said safety catheter comprising:

an elongated cylindrical member having a bore therethrough; and at least one retrieval member extending throughout said bore and extending from each end of said cylindrical member, a first portion of said retrieval member extending beyond an end of said cylindrical member terminating in an end having a greater diameter than said bore of said cylindrical member to prevent said end from entering said bore of said cylindrical member wherein said retrieval member maintains said bore of said cylindrical member open to allow said flow of said fluids to and from said body and the safe retrieval of said cylindrical member from said body and wherein said retrieval member comprises at least two elongated, solid members, each solid member terminating in a loop formed on said first portion of said retrieval member extending beyond an end of said cylindrical members to prevent passage of said first portion through said cylindrical member.

6. The safety catheter of claim 5, wherein said loops interlock.

* * * * *